US012063980B2

(12) United States Patent
Tidalgo

(10) Patent No.: US 12,063,980 B2
(45) Date of Patent: Aug. 20, 2024

(54) SYSTEM AND APPARATUS FOR INTELLIGENT VAPORIZER

(71) Applicant: Patrick Tidalgo, Aliso Viejo, CA (US)

(72) Inventor: Patrick Tidalgo, Aliso Viejo, CA (US)

( * ) Notice: Subject to any disclaimer, the term of this patent is extended or adjusted under 35 U.S.C. 154(b) by 403 days.

(21) Appl. No.: 17/515,559

(22) Filed: Nov. 1, 2021

(65) Prior Publication Data

US 2023/0138531 A1 May 4, 2023

(51) Int. Cl.
| | |
|---|---|
| A24F 40/53 | (2020.01) |
| A24F 40/10 | (2020.01) |
| A24F 40/42 | (2020.01) |
| A24F 40/51 | (2020.01) |
| A24F 40/65 | (2020.01) |
| A61M 11/04 | (2006.01) |

(52) U.S. Cl.
CPC .............. *A24F 40/53* (2020.01); *A24F 40/10* (2020.01); *A24F 40/42* (2020.01); *A24F 40/51* (2020.01); *A24F 40/65* (2020.01); *A61M 11/042* (2014.02); *A61M 2205/13* (2013.01); *A61M 2205/52* (2013.01); *A61M 2205/8206* (2013.01)

(58) Field of Classification Search
None
See application file for complete search history.

(56) References Cited

U.S. PATENT DOCUMENTS

| | | | | |
|---|---|---|---|---|
| 11,696,604 B2 * | 7/2023 | Henry, Jr. | ............... | A24F 40/53 |
| | | | | 131/328 |
| 11,696,988 B2 * | 7/2023 | Mizuguchi | ........... | A61M 11/042 |
| | | | | 128/200.14 |
| 11,809,542 B2 * | 11/2023 | Newcomb | ............... | A24F 40/40 |
| 11,825,877 B2 * | 11/2023 | Hatton | ................... | A24F 40/40 |
| 11,856,997 B2 * | 1/2024 | Sears | ...................... | A24F 40/40 |
| 2023/0108827 A1 * | 4/2023 | Johnson | .................. | A24F 40/42 |
| | | | | 131/329 |
| 2023/0115077 A1 * | 4/2023 | Chen | ..................... | G01F 23/266 |
| | | | | 131/329 |
| 2023/0292846 A1 * | 9/2023 | Henry, Jr. | ............... | A24F 40/53 |
| | | | | 131/328 |
| 2023/0301368 A1 * | 9/2023 | Moloney | ............. | A61M 15/009 |
| 2023/0380018 A1 * | 11/2023 | Bowen | ................. | A61M 11/042 |
| 2023/0413921 A1 * | 12/2023 | Sur | ........................ | A24F 40/57 |
| 2024/0016213 A1 * | 1/2024 | Atkins | .................... | A24F 40/46 |
| 2024/0032153 A1 * | 1/2024 | Cadieux | .................. | H05B 3/42 |

\* cited by examiner

*Primary Examiner* — Ross N Gushi
(74) *Attorney, Agent, or Firm* — Ying-Ting Chen; Law Office of Michael Chen

(57) ABSTRACT

An intelligent vaporizing system includes a vaporizing device having a cartridge detachably coupled with a main body, the cartridge includes: a container configured to receive a liquid; a sensor for detecting a user's action of inhalation; and a memory chip embedded inside the cartridge and communicated with the sensor, the memory chip configured to: record collected data from the sensor; receive associated data from an application; and transfer the collected data to the application; wherein the main body includes a heating element configured to heat the liquid to form a vaporized form; and a controller configured to receive the collected data and activate the heating element for heating the liquid.

20 Claims, 11 Drawing Sheets

SYSTEM AND APPARATUS FOR INTELLIGENT VAPORIZER

FIELD OF THE DISCLOSURE

The present disclosure relates to a system and apparatus for an intelligent vaporizer, and more particularly, the intelligent vaporizer may comprise a memory chip embedded inside cartridge which may be controlled by an application.

BACKGROUND OF THE DISCLOSURE

Generally, vaporizers or inhalers may be used to administer, transform or otherwise dispense a substance in a consumable format (i.e., vapor, fine powder, mist, liquid) for the user. One form of vaporizers includes electronic cigarettes. The substance for consumption through the vaporizer or inhalers may include CBD (Cannabidiol), THC (Tetrahydrocannabinol), vitamins, nicotine and nicotine quitting products, caffeine, melatonin and other herbal remedies (like echinacea or chamomille) or essential oils (like lavender or Orange oil), and more importantly prescription pharmaceutical medications.

Vaporizers configured for consumption by a user via inhaling may be operated through the use of various electronic components configured to heat the substance, wherein the substance may be stored as a liquid, to transform the liquid to a vapor phase for allowing the user's inhalation of the substance.

One non-limiting example of the vaporizers or inhalers associated with an application communicated with a server (database), the collected data may be transmitted and stored into the server. Even when the collected data may be stored into or transmitted to the server, it may cause several problems. For example, the collected data may not be delivered accurately and efficiently provided an up-to-date data content. For another example, the products' provided may spend large amounts of costs for the customer supports and communications in order to assure the customer's security and further accumulate brand loyalty customers.

In another non-limiting example, the conventional vaporizers or inhalers may not support the doctor or administrator to monitor or control the dosage of CBD (Cannabidiol), THC (Tetrahydrocannabinol), vitamins, nicotine and nicotine quitting products, caffeine, melatonin and other herbal remedies (like echinacea or chamomille) or essential oils (like lavender or Orange oil), and prescription pharmaceutical medications; and in such a situation, the drug abuse may be frequently happened without the doctor prescriptions.

There may exist a desire to develop a vaporizer or inhaler with a memory chip embedded inside the vaporizer or inhaler body in order to store/collect the collected data.

All referenced patents, applications and literatures are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The disclosed embodiments may seek to satisfy one or more of the above-mentioned desires. Although the present embodiments may obviate one or more of the above-mentioned desires, it should be understood that some aspects of the embodiments might not necessarily obviate them.

BRIEF SUMMARY OF THE DISCLOSURE

In a general implementation, an intelligent vaporizing system comprises a vaporizing device having a cartridge detachably coupled with a main body, the cartridge comprising: a container configured to receive a liquid; a sensor for detecting a user's action of inhalation; and a memory chip embedded inside the cartridge and communicated with the sensor, the memory chip configured to: record collected data from the sensor; receive associated data from an application; and transfer the collected data to the application; wherein the main body comprises: a heating element configured to heat the liquid to form a vaporized form; and a controller configured to receive the collected data and activate the heating element for heating the liquid.

In another aspect combinable with the general implementation, the main body comprises a display communicated with the memory chip, the display informing the associated data to a user.

In another aspect combinable with the general implementation, the memory chip comprises a cartridge ID, the cartridge ID corresponding to the associated data including types of liquid, brands of liquid, production date, expiration date, or batch number.

In another aspect combinable with the general implementation, the intelligent vaporizing system further comprises a server with a database stored therein, the database communicated with the application and configurated to store the associated data and the collected data transferring from the application.

In another aspect combinable with the general implementation, the collected data comprises puff count data, product data, date data, time data, or GPS location data, In another aspect combinable with the general implementation, the associated data comprises types of liquid, brands of liquid, production dates, expiration dates, batch numbers or maximum puff count data.

In another aspect combinable with the general implementation, the associated data causes the vaporizing device to modify settings of a cartridge ID stored in the memory chip; and set a maximum puff count data.

In another aspect combinable with the general implementation, the intelligent vaporizing system further comprises a managing device communicated with the application and configured to modify the associated data.

In another aspect combinable with the general implementation, the application changes settings of the vaporizing device, wherein the settings of the vaporizing device include lock/unlock the vaporizing device, power selections, or auto-rotation.

In another aspect combinable with the general implementation, the application communicates with a server, the server configured to receive or transmit an order from the application.

In another aspect combinable with the general implementation, the application causes the system to: set a dosage time limit corresponding to the liquid utilized by the main body; transmit puff count data to a server; and set a refresh time.

In another aspect combinable with the general implementation, the collected data causes the system to: deactivate the controller after a maximum puff count data is reached.

Another aspect of the embodiment is directed to an intelligent vaporizing device, comprising: a cartridge detachably coupled with a main body, the cartridge comprising: a container configured to receive a liquid; a sensor for detecting a user's action of inhalation; and a memory ship embedded inside the cartridge and communicated with the sensor; wherein the main body comprises: a heating element configured to heat the liquid to form a vaporized form; and a controller configured to activate the heating element for heating the liquid.

In another aspect combinable with the general implementation, the cartridge further comprises a communication unit communicated with and be controlled by an application running by a user device.

In another aspect combinable with the general implementation, the memory chip comprises a cartridge ID, the cartridge ID corresponding to associated data including types of liquid, brands of liquid, production dates, expiration dates, or batch numbers.

In another aspect combinable with the general implementation, the main body further comprises a display communicated with the memory chip, the display informing associated data to a user.

In another aspect combinable with the general implementation, the liquid may include CBD (Cannabidiol), THC (Tetrahydrocannabinol), vitamins, nicotine and nicotine quitting products, caffeine, melatonin and other herbal remedies (like echinacea or chamomille) or essential oils (like lavender or Orange oil), and prescription pharmaceutical medications.

In another aspect combinable with the general implementation, the main body further comprises a battery communicated with the display and the controller to provide a power source to the vaporizing device.

In another aspect combinable with the general implementation, the intelligent vaporizing device further comprises a power connector detachably engage with a proximal end of the main body.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above and below as acting in certain combinations and even initially claimed as such, one or more features from a claimed combination can in some cases be excised from the combination, and the claimed combination may be directed to a subcombination or variation of a subcombination.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

It should be noted that the drawing figures may be in simplified form and might not be to precise scale. In reference to the disclosure herein, for purposes of convenience and clarity only, directional terms such as top, bottom, left, right, up, down, over, above, below, beneath, rear, front, distal, and proximal are used with respect to the accompanying drawings. Such directional terms should not be construed to limit the scope of the embodiment in any manner.

DETAILED DESCRIPTION OF THE EMBODIMENTS

The different aspects of the various embodiments can now be better understood by turning to the following detailed description of the embodiments, which are presented as illustrated examples of the embodiments defined in the claims. It is expressly understood that the embodiments as defined by the claims may be broader than the illustrated embodiments described below.

The term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

It shall be understood that the term "means," as used herein, shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

Unless defined otherwise, all technical and position terms used herein have the same meaning as commonly understood by one of ordinary skill in the art to which the invention pertains. Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

Figure 1:
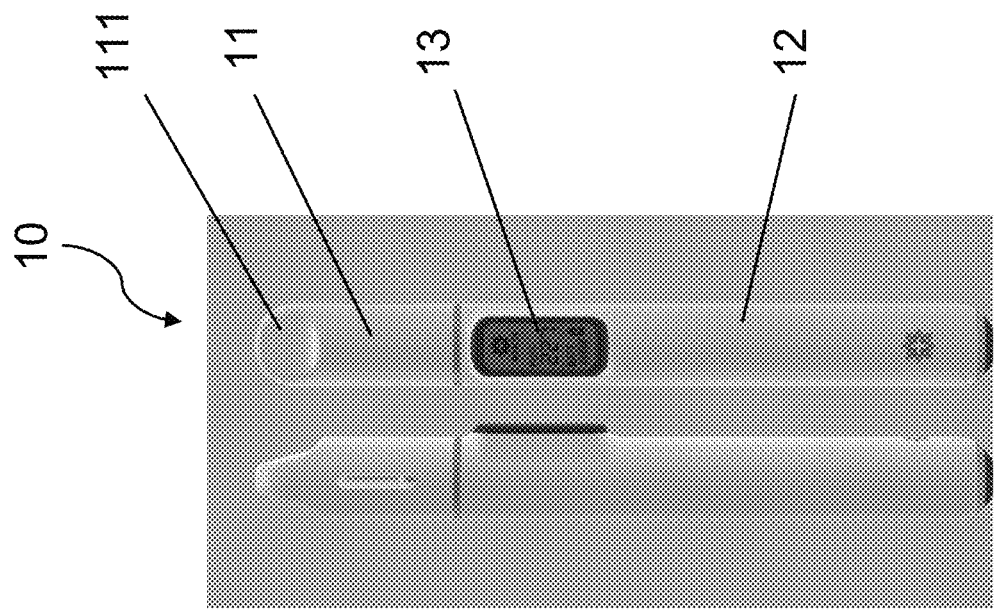
FIG. 1 is a perspective view of an embodiment of an intelligent vaporizing device according to an aspect of the embodiment.

FIG. 1 generally depicts views of an intelligent vaporizing device 10 according to an embodiment.

Referring to FIG. 1, the intelligent vaporizing device 10 comprises a cartridge 11, a main body 12 detachably coupled with the cartridge 11, a display 13 arranged on a surface of the main body 12.

In some embodiments, the cartridge 11 comprises a mouthpiece 111 formed on a distal end of the cartridge 11 and a proximal end of the cartridge 11 may be detachably coupled with a distal end of the main body 12.

Figure 2:
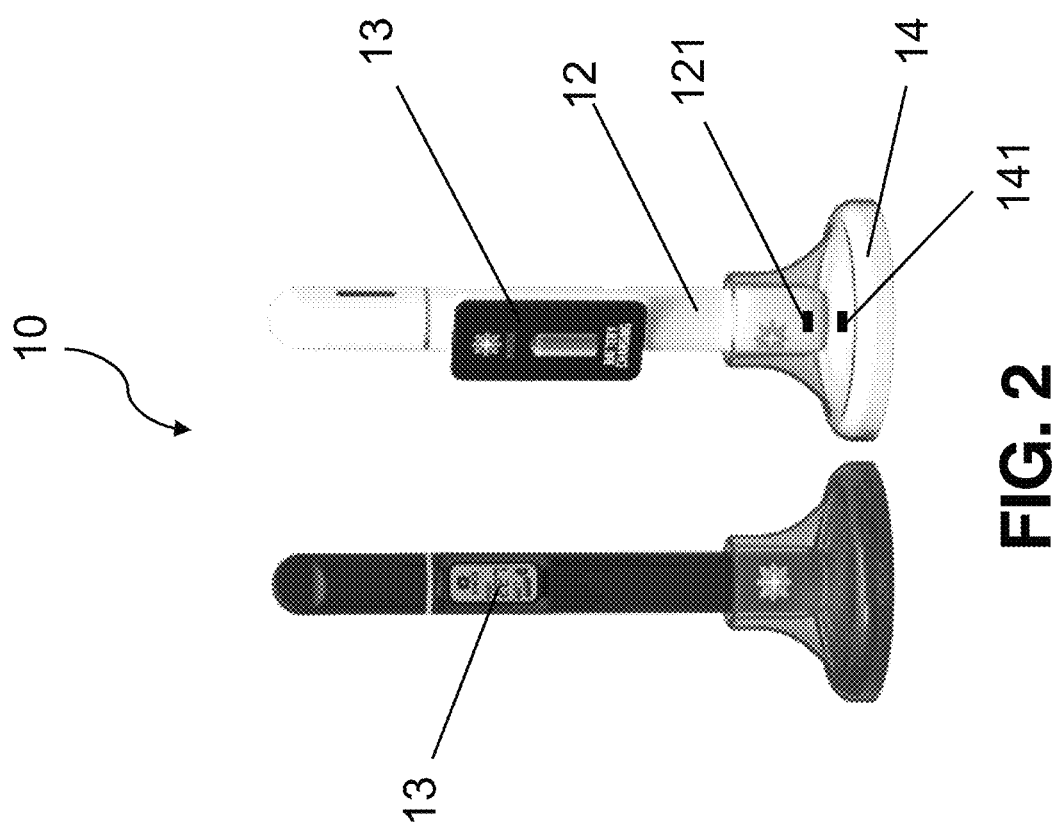
FIG. 2 is a perspective view of an embodiment of an intelligent vaporizing device incorporated with a power connector according to an aspect of the embodiment.

FIG. 2 generally depicts views of the intelligent vaporizing device 10 incorporated with a power connector 14 according to an embodiment.

Referring to FIG. 2, the intelligent vaporizing device 10 further comprises a power connector 14 detachably engage with a proximal end of the main body 12.

In some embodiments, the power connector 14 may be a magnetic connector having a male unit 141 magnetically coupled with a female unit 121 of the proximal end of the main body 12. It should be noted that the display 13 may be a LCD screen (Liquid Crystal Display) or an OLED (Organic Light-Emitting Diode). For example, the display 13 may include, e.g., thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g., stereoscopy, polarization filters, active shutters, or autostereoscopy.

It should be understood that the above-described displays 13 are exemplary, but is not limited to, and any other displays 13 can be adopted in various embodiments of this disclosure.

Figure 3:
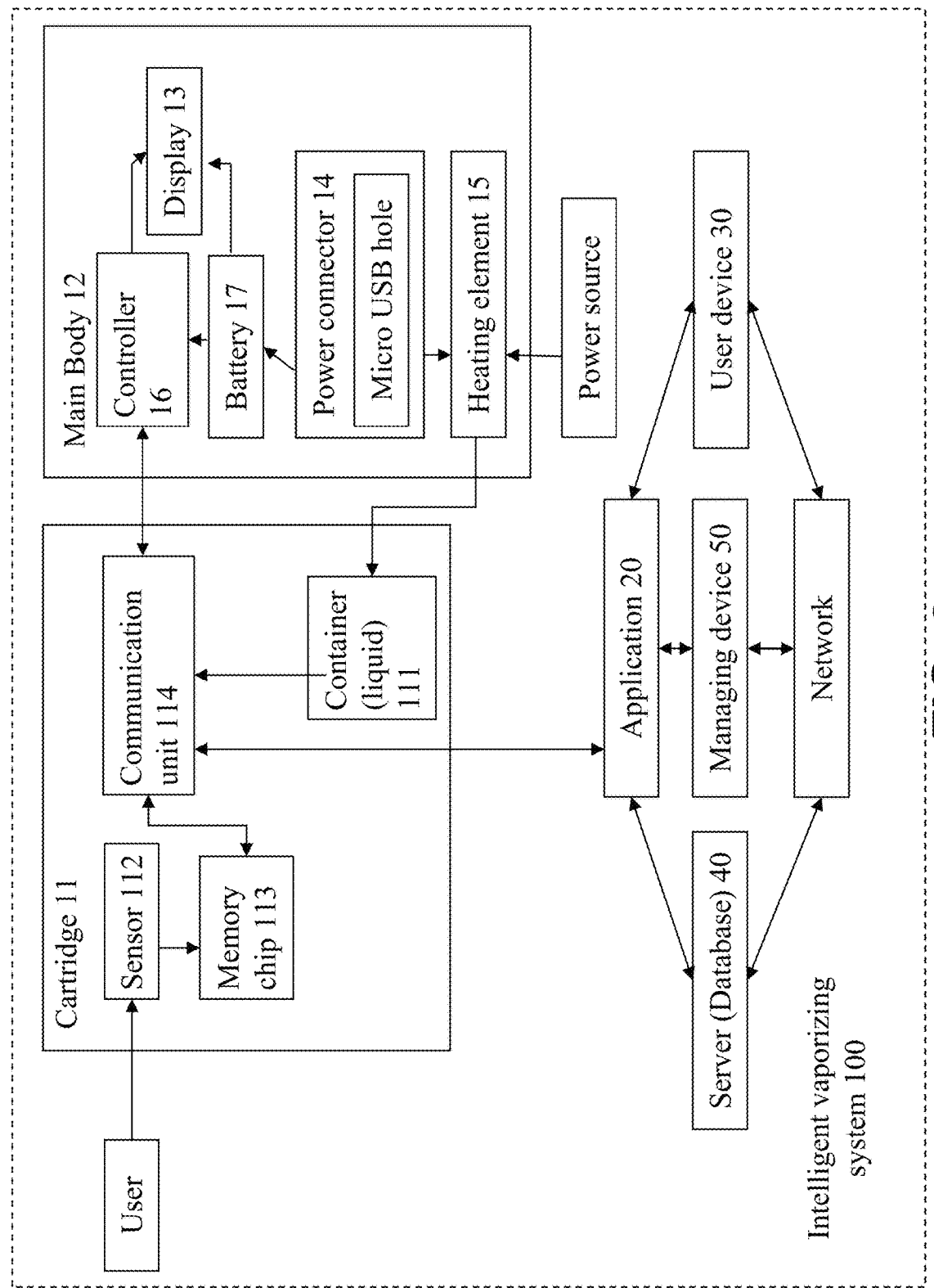
FIG. 3 is a block diagram of an embodiment of an intelligent vaporizing system according to an aspect of the embodiment.

FIG. 3 generally depicts a block diagram of an intelligent vaporizing system 100 according to an embodiment.

Referring to FIG. 3, the cartridge 11 further comprises a container 111 configured to receive a liquid, wherein the liquid may include CBD (Cannabidiol), THC (Tetrahydrocannabinol), series of CBD, sativa series of THC, hybrid series of THC, or indica series of THC, vitamins, nicotine and nicotine quitting products, caffeine, melatonin and other herbal remedies (like echinacea or chamomille) or essential oils (like lavender or Orange oil), and prescription pharmaceutical medications.

In some embodiments, the cartridge 11 further comprises a sensor 112 for detecting a user's action of inhalation and a memory chip 113 embedded inside the cartridge 11, wherein the memory chip 113 may be communicated with the sensor 112. The present memory chip 113 may also be configured to record collected data from the sensor 112.

In some embodiments, the main body 12 further comprises a battery 17 electrically connected to the power connector 14 for receiving a power source.

Figure 4:
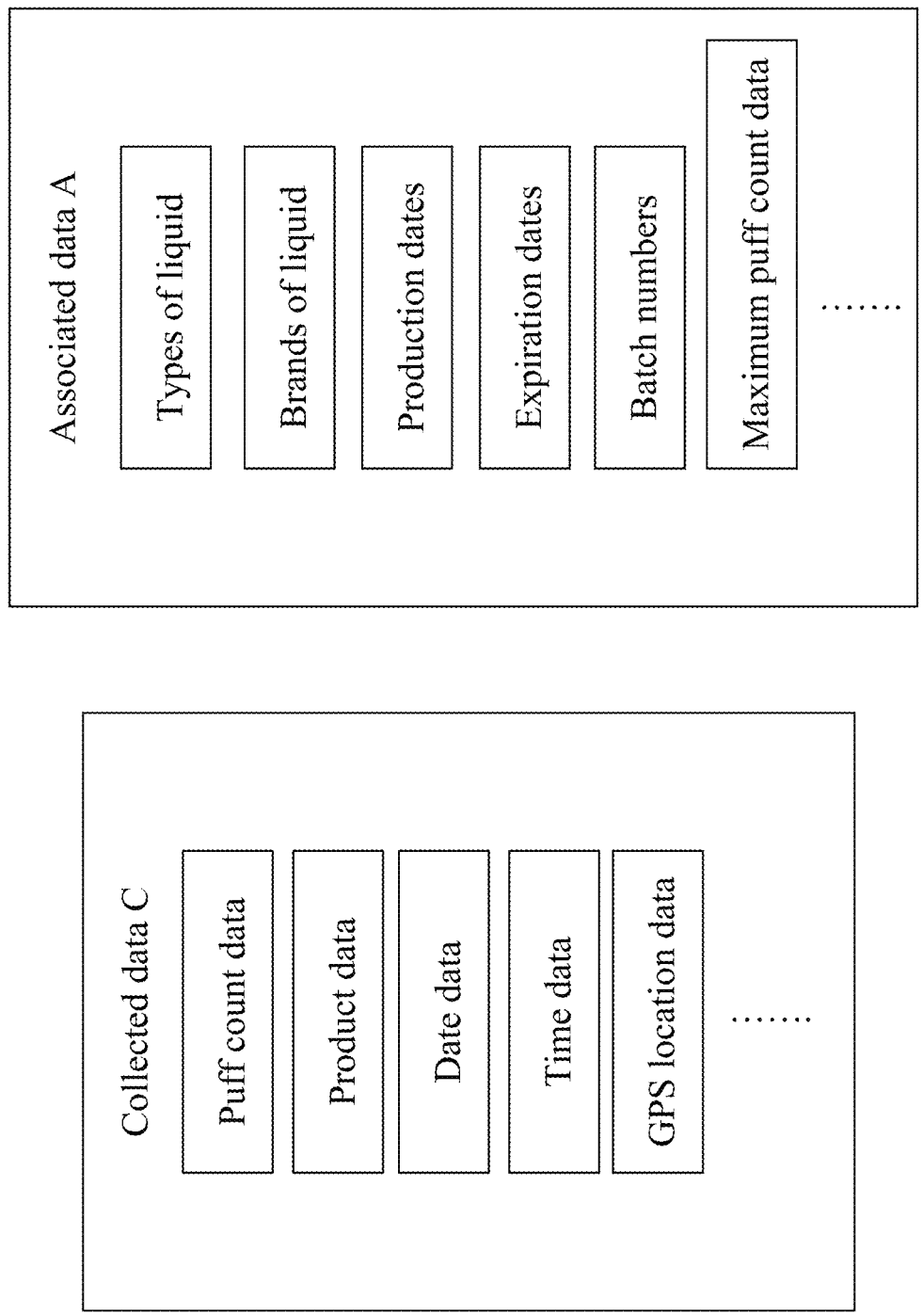
FIG. 4 is a block diagram of collected data and associated data according to an embodiment.

FIG. 4 generally depicts a block diagram of collected data and associated data according to an embodiment.

Referring to FIG. 4, the collected data C comprises puff count data, product data, date data, time data, or GPS location data, wherein the puff count data may be corresponding to an amount of puffs consumed by the user. The product data may be corresponding to types of liquid or brands of the liquid. The date data may be corresponding to the date of the user using the intelligent vaporizing device or the date of each puff consumed by the user. The time data may be corresponding to the overall time of the user using the intelligent vaporizing device or the overall time of the user using each puff. The GPS location data may be corresponding to the locations where the user uses the intelligent vaporizing device.

Turning to FIG. 3 and FIG. 4, in some embodiments, the memory chip 113 may be configured to receive associated data A from an application 20. Continuing to FIG. 3, for example, the intelligent vaporizing system 100 further comprises an application 20 communicated with the cartridge 11 of the intelligent vaporizing device, wherein the application 20 may be from an application distribution platform. Examples of application distribution platforms include the App Store for iOS provided by Apple, Inc., the Mac App Store provided by Apple, Inc., GOOGLE PLAY for Android OS provided by Google Inc., Amazon Appstore for Android OS or KINDLE FIRE provided by Amazon.com, Inc. An application distribution platform may facilitate installation of software on a user device. A user device 30 may select, purchase and/or download the application 20 via the application distribution platform.

It should be understood that the above-described application distribution platforms are exemplary but is not limited to and any other application distribution platforms can be adopted in various embodiments of this disclosure.

In some embodiments, the intelligent vaporizing system 100 further comprises a server 40 communicated with the application 20, wherein the server 40 serves as a database configured to store the collected data C, associated data A, and communication data, wherein the associated data A may be corresponding to a cartridge ID. For example, the associated data A includes types of liquid, brands of liquid, production dates, expiration dates, batch numbers or maximum puff count data (see details of FIG. 4).

In some embodiments, the cartridge 11 further comprises a communication unit 114 communicated with the application 20 running by the user device 30 to the communication data, wherein the application 20 changes device settings using the communication data. In known manner, the communication unit 114 may be coupled with the application 20 running by the user device 30 either through wireless or wired methods. For example, the communication data may comprise a means for the user to set security and/or authorization features of the user device 30, such as setting a PIN code to activate the user device 30 or the user's personal biometric information as a means of authentication.

In some embodiments, the memory chip 113 may cause the intelligent vaporizing system 100 to transmit the collected data C to the application 20, wherein the collected data C may be further transmitted to the server (database) 40 or the user device 30 and to be stored in the server 40.

In some embodiments, the intelligent vaporizing system 100 further comprises a managing device 50 communicated with the application 20, wherein the managing device 50 may be configured to prescribe a certain dosage for the patient, such as usage limits or alarms. For example, the usage limits can be set to not exceed the suggested usage based on the frequency or time limit. For another example, the alarms can be set to inform the patient to start a medical session. It should be noted that the medical session may include a number of sessions per day, an amount of puffs per medical session, or time for the next medical session.

In some embodiments, the managing device 50 may be configured to modify the associated data A or the collected data C saved in the server 40 or running by the application 20. For example, the associated data A or the collected data C may be outputted to form in certain files, such as XLS, CSV, XML, or other spreadsheet formats, and the doctor or administrator may modify the associated data A or the collected data C by accessing an account via Internet (wireless links).

With specific reference to FIG. 3, the main body 12 of the intelligent vaporizing device further comprises a heating element 15 configured to heat the liquid to form a vaporized form, wherein the heating element 15 may be communicated with the container 111, and in such a way, the heating element 15 may generate a heating source to heat the liquid.

In some embodiments, the main body 12 further comprises a controller 16 electrically connected with the communication unit 114 and the heating element 15, wherein the controller 16 may be configured to receive the collected data and to activate the heating element 15 for heating the liquid. It should be noted that the controller 16 may be also configured to deactivate the heating element 15 in order to lock the intelligent vaporizing device.

In some embodiments, the main body 12 further comprises the display 13 electrically connected with the controller 16, wherein the controller 16 may be electrically connected with the memory chip 113. The display 13 also features for informing the associated data to the user.

Figure 5:
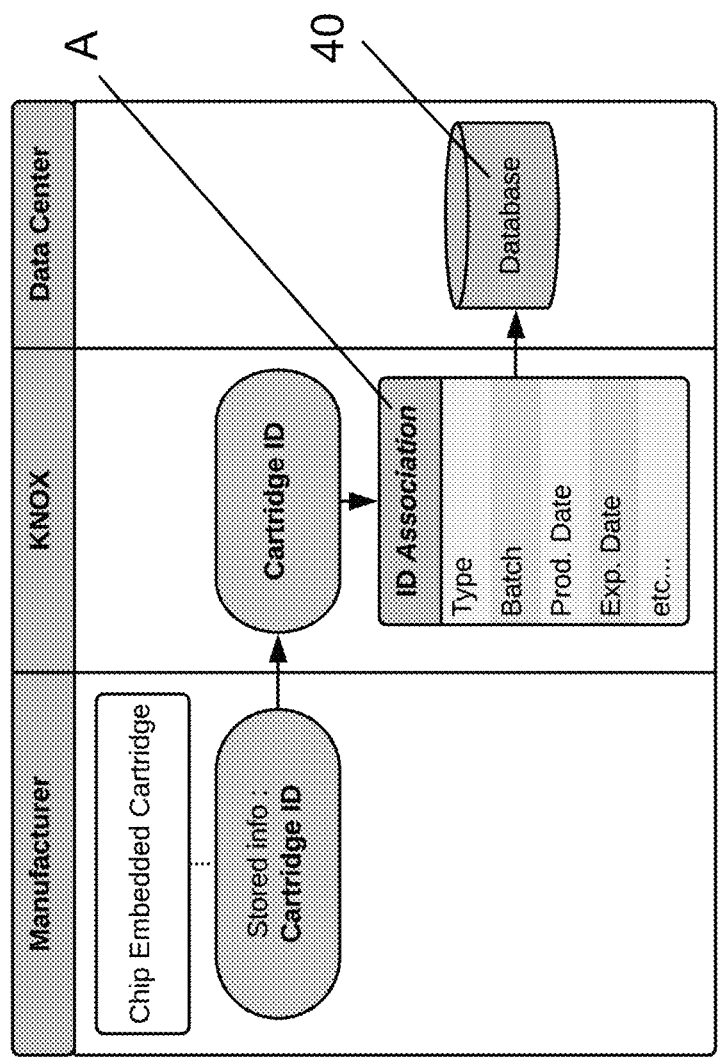
FIG. 5 is a block diagram of a method of a cartridge initialization process according to an aspect of the embodiment.

FIG. 5 generally depicts a block diagram of a cartridge initialization process for the intelligent vaporizing system according to an embodiment.

Referring to FIG. 5, it should be noted that the memory chip may be pre-embedded inside the cartridge by manufacturers. For example, the memory chip comprises the cartridge ID, and the cartridge ID may be corresponding to the associated data A including types of liquid, brands of liquid, production dates, expiration dates, batch numbers or maximum puff count data (see details in FIG. 4). In a known manner, the cartridge ID may be corresponding to the associated data A saved in the database (server) 40. In other words, the cartridge ID may be synchronized with the associated data A saved in the database (server) 40.

In some embodiments, the database (server) 40 may be electrically connected with the application 20 electrically connected with the managing device 50 (see details in FIG. 3), and in such a manner, the managing device 50 may be used to modify the cartridge ID by modifying the associated data saved in the database (server) 40.

In some embodiments, the database (server) 40 may be electrically connected with application 20 electrically connected with the managing device 50, and in such a manner, the managing device 50 may be used to modify the associated data saved in the memory chip 113 by modifying settings of the cartridge ID (see details in FIG. 3).

Accordingly, the types of liquid, the brands of liquid, the production dates, the expiration dates may be updated by modifying the associated data A or the collected data C saved in either the memory chip 113 or the server (database) 40. In the known manner, the associated data A or the collected data C may be transmitted to the application 20 and then may be modified by the managing device 50 or the administrator. In some embodiments, the maximum puff count data may be set by modifying the associated data A or the collected data C saved either in the memory chip 113 or the server (database) 40 (see details in FIGS. 3 and 4).

Figure 6:
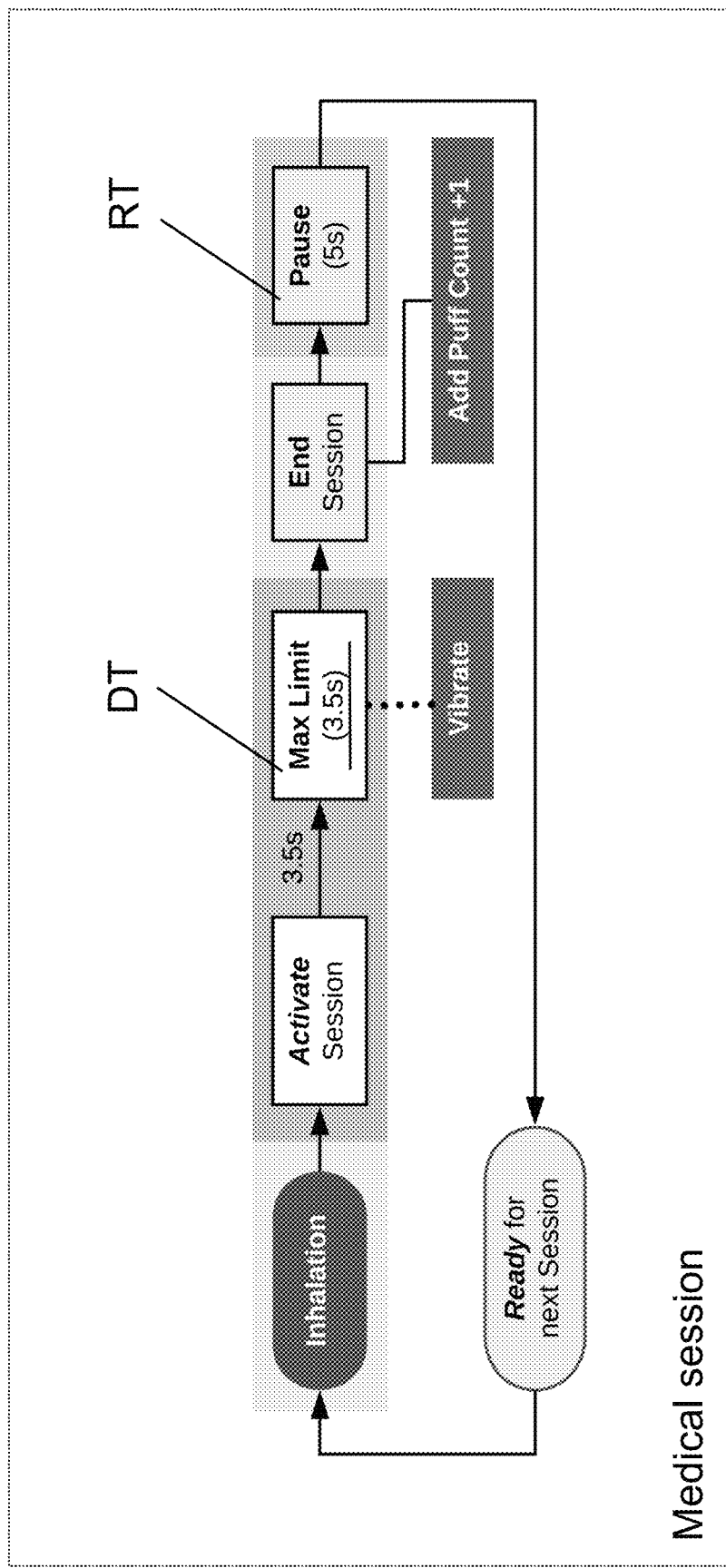
FIG. 6 is a block diagram of a process for automatically activating the intelligent vaporizing device in per medical session according to the embodiment.

FIG. 6 generally depicts a block diagram of a process for automatically activating the intelligent vaporizing device in per medical session according to an embodiment.

Referring to FIG. 6, the intelligent vaporizing device may be automatically activated by an inhalation and the associated data saved in the memory chip may cause the intelligent vaporizing device to set a dosage time limit DT corresponding to the liquid utilized by the main body. For example, the dosage time limit DT may be 3.5 seconds. While the dosage time reaches to the dosage time limit DT, the vaporizer body may send a vibrating pulse to inform the user that a medical session may be completed. And then, the medical session may be ended, and the puff count data may be transmitted to the server (database) 40 (see details in FIG. 3). Continuingly, the associated data may set a refresh time RT (a predetermined pause time) in order to start the next medical session. For example, the refresh time RT may be 5 seconds to 10 seconds.

In some embodiments, the dosage time limit DT and the refresh time RT may be changeable by the application 20 running by the user's device 30 or the managing device 50 (see details in FIG. 3).

Figure 7:
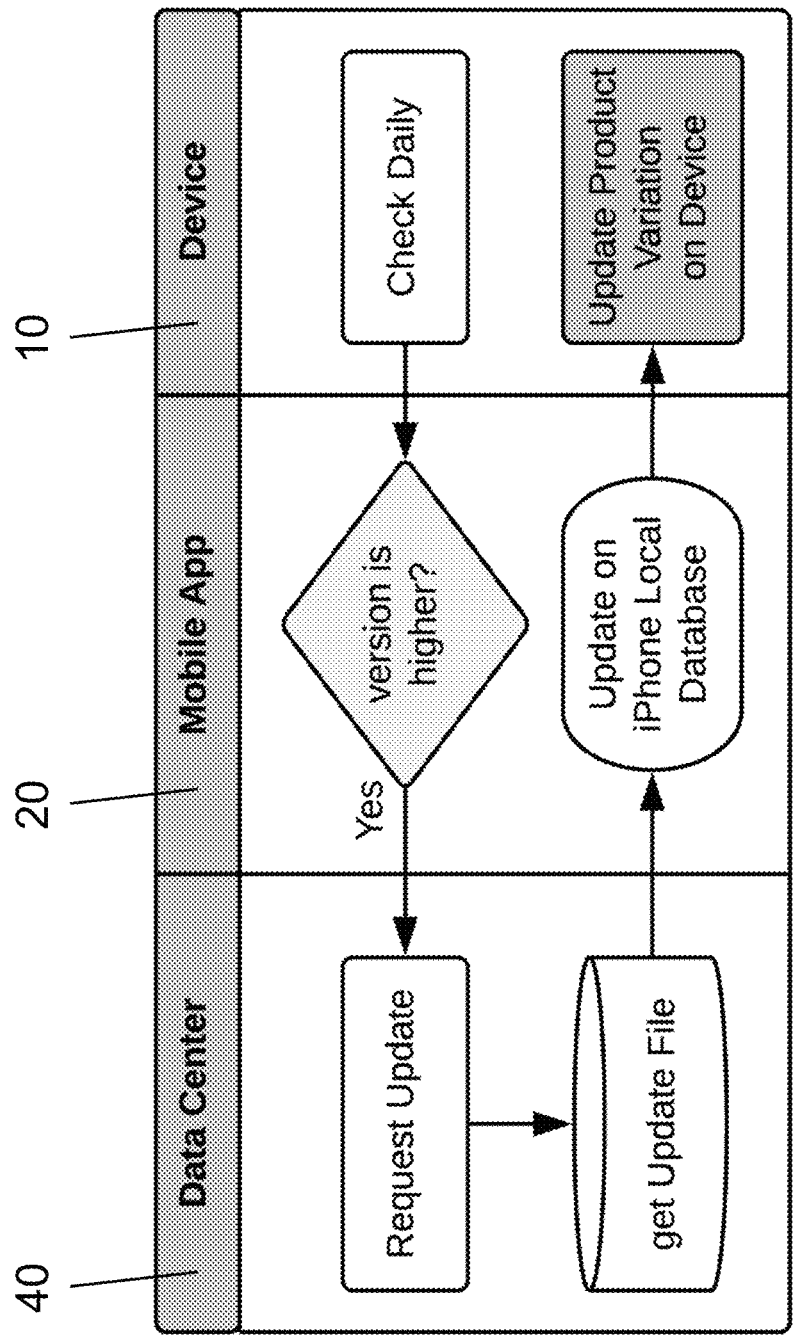
FIG. 7 is a block diagram of a process for automatically updating the intelligent vaporizing device according to the embodiment.

FIG. 7 generally depicts a block diagram of a process for automatically updating the intelligent vaporizing device according to the embodiment.

Referring to FIG. 7, the intelligent vaporizing device 10 may be synchronized with the application 20, and the intelligent vaporizing device 10 may perform a daily check in order to assure a software version being satisfied. When the software version may be higher than the version running on the application 20, the database (server) 40 may be activated to send an update data to the application 20 to modify the software version running thereby, and in such a way, the updated software version may comprise updated product variations.

Figure 8:
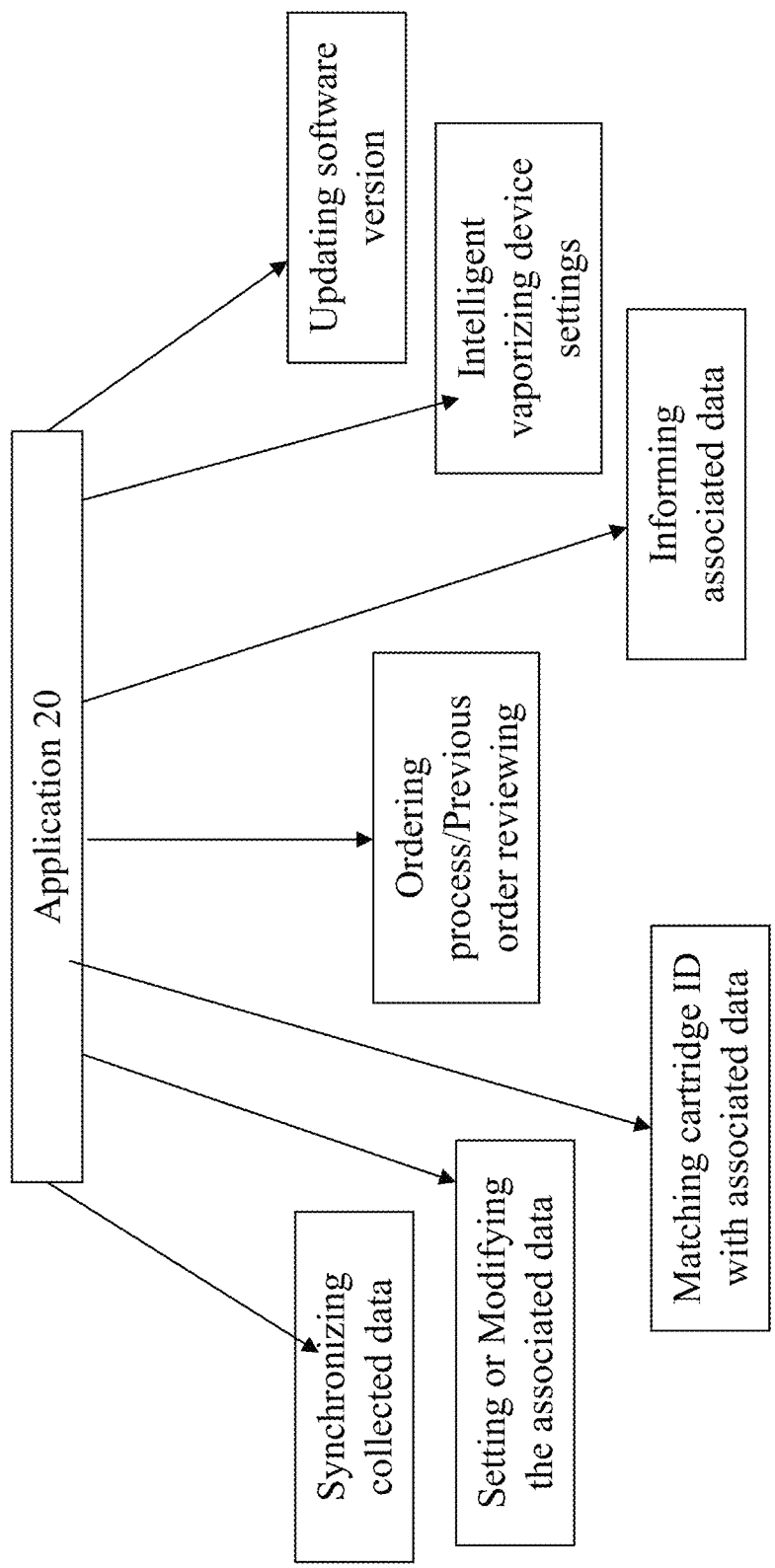
FIG. 8 is a block diagram of a program running by the application for the intelligent vaporizing system according to the embodiment.

FIG. 8 generally depicts a block diagram of a program running by the application for the intelligent vaporizing system according to the embodiment.

Referring to FIG. 8, the application 20 servers as a program having functions which may cause the system to: a. sync collected data b. match the cartridge ID with the associated data c. place an order and review previous ordering history d. set up settings for the intelligent vaporizing device e. update software version f. set or modify the associated data.

It should be understood that the above-described functions is disclosed but is not limited to and any other functions can be adopted in various embodiments of this disclosure.

In some embodiments, the application 20 may communicate with the server and may cause the system to receive or transmit an order from the application to the server (database). Here, the application 20 may be utilized to review the previous ordering status or check the delivering status of the orderings. It should be noted that in some embodiments the user may modify or update the orderings through the application 20 or directly place the orders from the user device.

In some embodiments, the application 20 may cause the system to set or modify the associated data saved on the memory chip of the intelligent vaporizing device. For example, the application 20 may cause the system to set up the maximum puff count data for the intelligent vaporizing device. When the maximum puff count data is reached, the controller may be deactivated to lock the intelligent vaporizing device.

Figure 9:
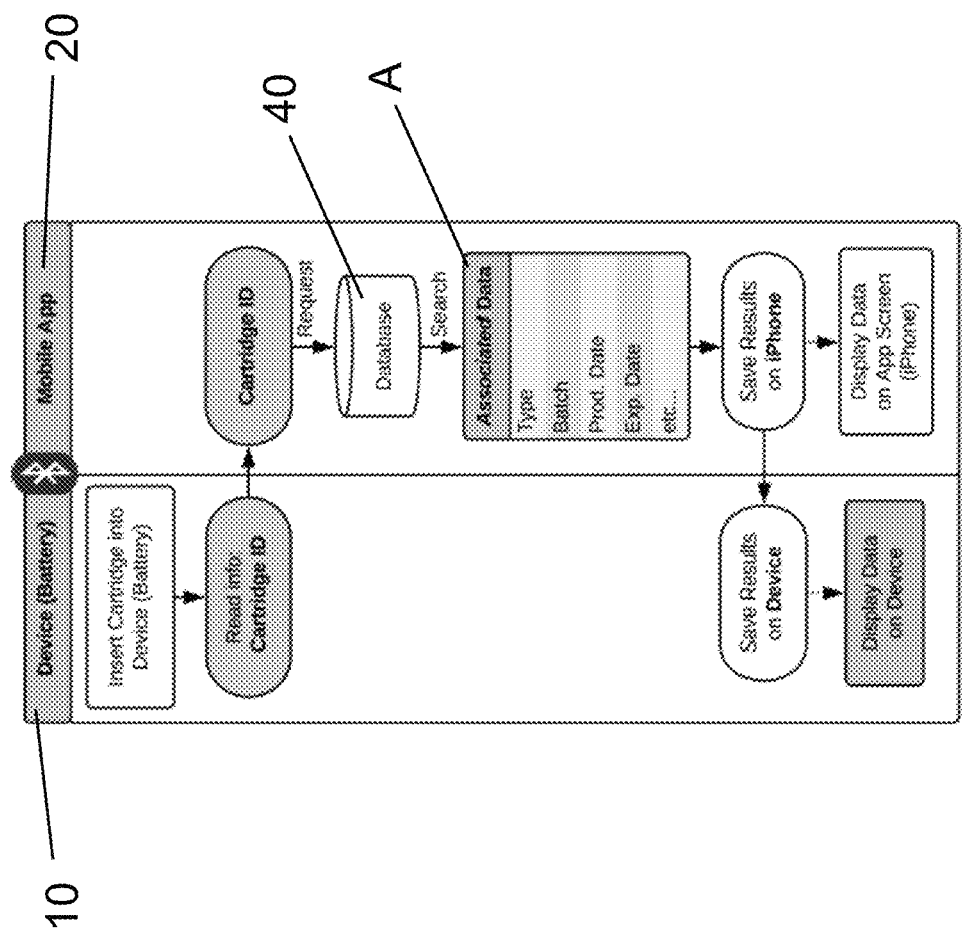
FIG. 9 is a block diagram of a method to match the cartridge ID with the associated data for the intelligent vaporizing system according to the embodiment.

FIG. 9 generally depicts a block diagram of a method to match the cartridge ID with the associated data A for the intelligent vaporizing system according to the embodiment.

Referring to FIG. 9, the method includes steps of:
- inserting the cartridge into the main body;
- reading from and transmitting the cartridge ID to the application 20;
- sending a request to the database (server) 40;
- searching the database 40 and finding the associated data A corresponding to the cartridge ID;
- saving the associated data A on the application 20; and
- displaying the associated data A on a screen incorporated with the user device.

In some embodiments, the application 20 may be running by the user device 30 or the managing device 50 (see details in FIG. 3), wherein the screen may be incorporated with the user device 30 or the managing device 50. For example, the associated data A may be informed to the user through the user device 30 or informed to the doctor or the administrator by the managing device 50.

Figure 10:
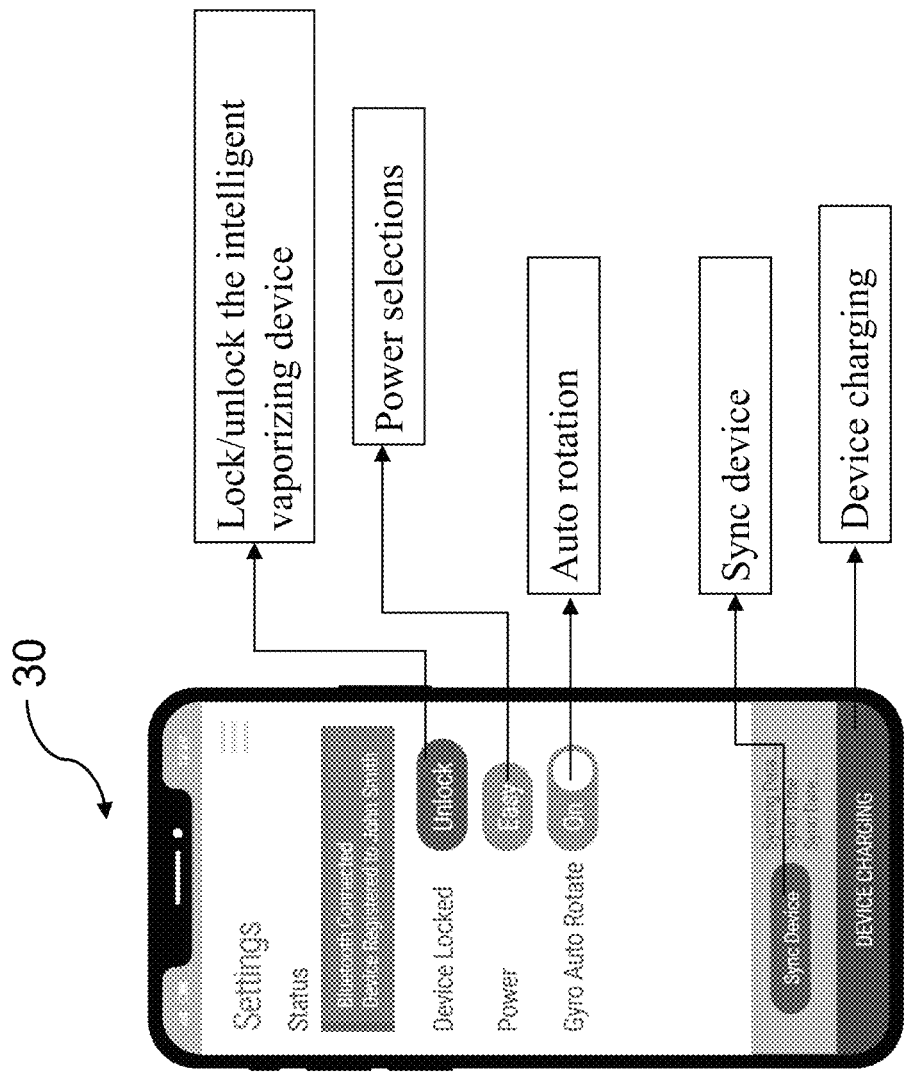
FIG. 10 is a front view of the display incorporated by the user device for the intelligent vaporizing system according to the embodiment.

FIG. 10 generally depicts views of the screen incorporated by the user device 30 for the intelligent vaporizing system according to the embodiment.

Referring to FIG. 10, the application may cause the system to set up settings for the intelligent vaporizing device. For example, the settings may comprise lock/unlock the intelligent vaporizing device, power selections, auto rotation, sync device, or device charging. For example, the intelligent vaporizing device may be lock or unlock through the application, wherein a means of lock or unlock the intelligent vaporizing device 10 may cause activate or deactivate the controller of the main body. For another example, the power selections may comprise a slow energy mode, an easy energy mode, or a high energy mode, wherein the slow energy mode may consume less battery power than the easy energy mode and the high energy mode. In other words, the easy energy mode may consume less battery power than the high energy mode. For another example, the auto rotation may be turned on to allow the screen to auto-rotate while viewing the screen, and in other words, the auto rotation may be turned off to forbid the auto-rotation of the screen. For another example, the sync device may be turned off and to stop the synchronization between the application and the intelligent vaporizing device. For another example, the intelligent vaporizing device may be automatically synchronized with the application. For another example, the device charging may be pressed to deactivate the charging of the intelligent vaporizing device.

Figure 11:
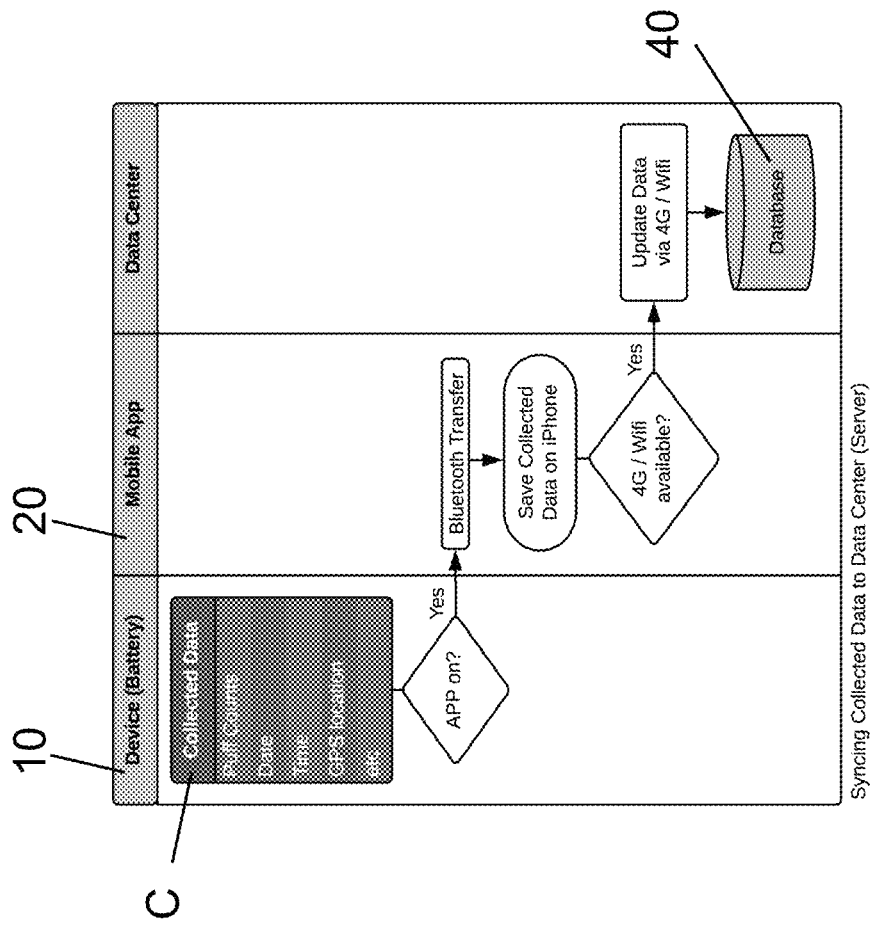
FIG. 11 is a block diagram of a method for synchronizing the collected data with the database (server) for the intelligent vaporizing system according to the embodiment.

FIG. 11 generally depicts a block diagram of a method for synchronizing the collected data C with the database (server) 40 for the intelligent vaporizing system according to the embodiment.

Referring to FIG. 11, the collected data C may be transmitted to the database (server) 40 through the application 20. For example, the application 20 may be used to synchronize the collected data C with the database (server) 40 in order to update the data saved on the database (server) 40.

In some embodiments, the method for synchronizing the collected data C with the database (server) 40 comprises steps of:
- collecting the collected data C;
- detecting/connecting the intelligent vaporizing device 10 with the application 20;
- transmitting the collected data C to the application 20;
- saving the collected data C on the application 20; and
- transmitting the collected data C to the database (server) 40.

In some embodiments, the application 20 may be connected with the database (server) 40 via wireless links. The wireless links may include BLUETOOTH, Wi-Fi, NFC, RFID Worldwide Interoperability for Microwave Access (WiMAX), an infrared channel or satellite band. The wireless links may also include any cellular network standards used to communicate among mobile devices, including standards that qualify as 1G, 2G, 3G, or 4G.

It should be understood that the above-described wireless links is disclosed, but is not limited to, and any other wireless links can be adopted in various embodiments of this disclosure.

Many alterations and modifications may be made by those having ordinary skill in the art without departing from the spirit and scope of the disclosed embodiments. Therefore, it must be understood that the illustrated embodiments have been set forth only for the purposes of example and that it should not be taken as limiting the embodiments as defined by the following claims. For example, notwithstanding the fact that the elements of a claim are set forth below in a certain combination, it must be expressly understood that the embodiment includes other combinations of fewer, more or different elements, which are disclosed herein even when not initially claimed in such combinations.

Thus, specific embodiments and applications of system and device for intelligent vaporizer have been disclosed. It should be apparent, however, to those skilled in the art that many more modifications besides those already described are possible without departing from the disclosed concepts herein. The disclosed embodiments, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the embodiments. In addition, where the specification and claims refer to at least one of something selected from the group consisting of A, B, C . . . and N, the text should be interpreted as requiring at least one element from the group which includes N, not A plus N, or B plus N, etc.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims therefore include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

What is claimed is:

1. An intelligent vaporizing system, comprising:
a vaporizing device having a cartridge detachably coupled with a main body, the cartridge comprising:
  a container configured to receive a liquid;
  a sensor for detecting a user's action of inhalation; and
  a memory chip embedded inside the cartridge and communicated with the sensor, the memory chip configured to:
    record collected data from the sensor;
    receive associated data from an application; and
    transfer the collected data to the application; wherein
the main body comprises:
  a heating element configured to heat the liquid to form a vaporized form; and
  a controller configured to receive the collected data and activate the heating element for heating the liquid.

2. The intelligent vaporizing system of claim 1, wherein the main body comprises a display communicated with the memory chip, the display informing the associated data to a user.

3. The intelligent vaporizing system of claim 1, wherein the memory chip comprises a cartridge ID, the cartridge ID corresponding to the associated data.

4. The intelligent vaporizing system of claim 1, further comprising a server with a database stored therein, the server communicated with the application and configured to store the associated data and the collected data transmitting from the application.

5. The intelligent vaporizing system of claim 1, wherein the collected data comprises puff count data, product data, date data, time data, or GPS location data.

6. The intelligent vaporizing system of claim 1, wherein the associated data comprises types of liquid, brands of liquid, production dates, expiration dates, batch numbers or maximum puff count data.

7. The intelligent vaporizing system of claim 1, wherein the associated data causes the vaporizing device to:
modify settings of a cartridge ID stored in the memory chip; and
set maximum puff count data.

8. The intelligent vaporizing system of claim 1, further comprises a managing device communicated with the application and configured to modify the associated data.

9. The intelligent vaporizing system of claim 1, wherein the application changes settings of the vaporizing device, wherein the settings of the vaporizing device include lock or unlock the vaporizing device, power selections, or auto-rotation.

10. The intelligent vaporizing system of claim 1, wherein the application communicates with a server, the server configured to receive an order from the application.

11. The intelligent vaporizing system of claim 1, wherein the application causes the system to:
set a dosage time limit corresponding to the liquid utilized by the main body;
transmit puff count data to a server; and
set a refresh time.

12. The intelligent vaporizing system of claim 1, wherein the collected data causes the system to:
deactivate the controller with maximum puff count data being reached.

13. The intelligent vaporizing device of claim 1, wherein the liquid comprises CBD (Cannabidiol), THC (Tetrahydrocannabinol), vitamins, nicotine and nicotine quitting products, caffeine, melatonin and other herbal remedies (like echinacea or chamomille) or essential oils (like lavender or Orange oil), and prescription pharmaceutical medications.

14. An intelligent vaporizing device, comprising:
a cartridge detachably coupled with a main body, the cartridge comprising:
  a container configured to receive a liquid;
  a sensor for detecting a user's action of inhalation; and
  a memory chip embedded inside the cartridge and communicated with the sensor; wherein
the main body comprises:
  a heating element configured to heat the liquid to form a vaporized form; and
  a controller configured to activate the heating element for heating the liquid.

15. The intelligent vaporizing device of claim 14, wherein the cartridge further comprises a communication unit communicated with and be controlled by an application running by a user device.

16. The intelligent vaporizing device of claim 14, wherein the memory chip comprises a cartridge ID, the cartridge ID corresponding to associated data including types of liquid, brands of liquid, production dates, expiration dates, or batch numbers.

17. The intelligent vaporizing device of claim 14, wherein the main body further comprises a display communicated with the memory chip, the display informing associated data to a user.

18. The intelligent vaporizing device of claim 14, wherein the liquid comprises CBD (Cannabidiol), THC (Tetrahydrocannabinol), vitamins, nicotine and nicotine quitting products, caffeine, melatonin and other herbal remedies (like echinacea or chamomille) or essential oils (like lavender or Orange oil), and prescription pharmaceutical medications.

19. The intelligent vaporizing device of claim 14, wherein the main body further comprises a battery communicated with the display and the controller to provide a power source to the vaporizing device.

20. The intelligent vaporizing device of claim 14, further comprising a power connector detachably engage with a proximal end of the main body.

* * * * *